United States Patent
Dunn et al.

(10) Patent No.: US 12,040,080 B2
(45) Date of Patent: Jul. 16, 2024

(54) DEEP LEARNING SYSTEM FOR DIFFERENTIAL DIAGNOSIS OF SKIN DISEASES

(71) Applicant: Google LLC, Mountain View, CA (US)

(72) Inventors: Robert Carter Dunn, San Carlos, CA (US); Ayush Jain, Los Altos, CA (US); Peggy Yen Phuong Bui, San Francisco, CA (US); Clara Eng, San Carlos, CA (US); David Henry Way, Redwood City, CA (US); Kang Li, Sunnyvale, CA (US); Vishakha Gupta, Sunnyvale, CA (US); Jessica Gallegos, San Francisco, CA (US); Dennis Ai, Redwood City, CA (US); Yun Liu, Mountain View, CA (US); David Coz, Mountain View, CA (US); Yuan Liu, Santa Clara, CA (US)

(73) Assignee: GOOGLE LLC, Mountain View, CA (US)

( * ) Notice: Subject to any disclaimer, the term of this patent is extended or adjusted under 35 U.S.C. 154(b) by 384 days.

(21) Appl. No.: 17/620,445

(22) PCT Filed: Sep. 11, 2020

(86) PCT No.: PCT/US2020/050472
§ 371 (c)(1),
(2) Date: Dec. 17, 2021

(87) PCT Pub. No.: WO2021/050928
PCT Pub. Date: Mar. 18, 2021

(65) Prior Publication Data
US 2022/0359062 A1    Nov. 10, 2022

Related U.S. Application Data

(60) Provisional application No. 62/898,835, filed on Sep. 11, 2019.

(51) Int. Cl.
*G16H 30/40* (2018.01)
*G16H 10/60* (2018.01)
*G16H 50/20* (2018.01)

(52) U.S. Cl.
CPC .............. *G16H 30/40* (2018.01); *G16H 10/60* (2018.01); *G16H 50/20* (2018.01)

(58) Field of Classification Search
CPC ........ G16H 30/40; G16H 10/60; G16H 50/20; G16H 30/20
(Continued)

(56) References Cited

U.S. PATENT DOCUMENTS 10,878,567 B1 * 12/2020 Abid ...................... G16H 40/63
2012/0008838 A1     1/2012 Guyon et al.

FOREIGN PATENT DOCUMENTS

| CN | 108198620 | 6/2018 |
| EP | 2733644 | 11/2012 |
| WO | WO 2016/033405 | 3/2016 |

OTHER PUBLICATIONS

Agency for Healthcare Research and Quality, "The Distribution of the U.S. Primary Care Workforce", https://www.ahrq.gov/research/findings/factsheets/primary/pcwork3/index.html, 2012, retrieved on May 11, 2022, 1 page.

(Continued)

Primary Examiner — Charlotte M Baker
(74) Attorney, Agent, or Firm — DORITY & MANNING P.A.

(57) ABSTRACT

The present disclosure is directed to a deep learning system for differential diagnoses of skin diseases. In particular, the system performs a method that can include obtaining a plurality of images that respectively depict a portion of a patient's skin. The method can include determining, using a machine-learned skin condition classification model, a plu- (Continued)

rality of embeddings respectively for the plurality of images. The method can include combining the plurality of embeddings to obtain a unified representation associated with the portion of the patient's skin. The method can include determining, using the machine-learned skin condition classification model, a skin condition classification for the portion of the patients skin, the skin condition classification produced by the machine-learned skin condition classification model by processing the unified representation, wherein the skin condition classification identifies one or more skin conditions selected from a plurality of potential skin conditions.

20 Claims, 11 Drawing Sheets

(58) Field of Classification Search
USPC .......................................................... 382/128
See application file for complete search history.

(56) References Cited

OTHER PUBLICATIONS

Awadall et al., "Dermatologic Disease in Family Medicine", Family Medicine-Kansas City, vol. 40, No. 7, 2008, pp. 507-511.
Aysa, https://askaysa.com/, retrieved on May 9, 2022, 8 pages.
Barnett et al., "Comparative Accuracy of Diagnosis by Collective Intelligence of Multiple Physicians vs Individual Physicians", JAMA Network Open, vol. 2, 2019, 11 pages.
Brinker et al., "Deep learning outperformed 136 of 157 dermatologists in a head-to-head dermoscopic melanoma image classification task", European Journal of Cancer, vol. 113, 2019, pp. 47-54.
Chihara et al., "Mathematical Statistics with Resampling and R", Wiley Online Library, 2018, 30 pages.
Codella et al., "Skin lesion analysis toward melanoma detection: A challenge at the 2017 International symposium on biomedical imaging (ISBI), hosted by the international skin imaging collaboration (ISIC)", arXiv:1710.05006v3, https://arxiv.org/abs/1710.05006, 5 pages.
Collins et al., "Transparent Reporting of a multivariable prediction model for Individual Prognosis or Diagnosis (TRIPOD): the TRIPOD Statement", British Journal of Surgery, vol. 102, No. 3, 2015, pp. 148-158.
Cruz-Roa et al., "A Deep Learning Architecture for Image Representation, Visual Interpretability and Automated Basal-Cell Carcinoma Cancer Detection", Medical Image Computing and Computer-Assisted Intervention—MICCAI 2013, Lecture Notes in Computer Science, vol. 8150, pp. 403-410.
Cutrone et al., "Dermatological image search engines on the Internet: do they work?", Journal of the European Academy of Dermatology and Venereology, vol. 21, No. 2, 2006, pp. 175-177.
Dean et al., "Large Scale Distributed Deep Networks", Advances in Neural Information Processing Systems 25, 2012, pp. 1223-1231.
Esteva et al., "Dermatologist-level classification of skin cancer with deep neural networks", Nature 542, 2017, pp. 115-118.
Federman et al., "Comparison of Dermatologic Diagnoses by Primary Care Practitioners and Dermatologists", Archives of Family Medicine, vol. 8, 1999, pp. 170-172.
Feng et al., "Comparison of Dermatologist Density Between Urban and Rural Counties in the United States", JAMA Dermatology, vol. 154, No. 11, 2018, pp. 1265-1271.
First Derm, https://www.firstderm.com/ai-dermatology/, retrieved on May 9, 2022, 5 pages.
Guyatt et al., "Users' Guides to the Medical Literature: A Manual for Evidence-Based Clinical Practice", Journal of the Medical Library Association, vol. 90, No. 4, 2002, pp. 482-483.
Haenssle et al., "Man against machine: diagnostic performance of a deep learning convolutional neural network for dermoscopic melanoma recognition in comparison to 58 dermatologists", Annals of Oncology, 2018, pp. 1836-1842.
Hahn, "Understanding noninferiority trials", Korean Journal of Pediatrics, vol. 55, 2012, pp. 403-407.
Han et al., "Classification of the Clinical Images for Benign and Malignant Cutaneous Tumors Using a Deep Learning Algorithm", Journal of Investigative Dermatology, vol. 138, No. 7, 2018, pp. 1529-1538.
Han et al., "Deep neural networks show an equivalent and often superior performance to dermatologists in onychomycosis diagnosis: Automatic construction of onychomycosis datasets by region-based convolutional deep neural network", Plos One, 2018, 14 pages.
Hay et al., "The Global Burden of Skin Disease in 2010: An Analysis of the Prevalence and Impact of Skin Conditions", Journal of Investigative Detmatology, vol. 134, No. 6, 2014, pp. 1527-1534.
International Preliminary Report on Patentability for Application No. PCT/US2020/050472, dated Mar. 24, 2022, 8 pages.
International Search Report and Written Opinion for Application No. PCT/US2020/050472, dated Dec. 8, 2020, 11 pages.
Ioffe et al., "Batch Normalization: Accelerating Deep Network Training by Reducing Internal Covariate Shift", arXiv:1502.03167v3, https://arxiv.org/abs/1502.03167, 11 pages.
Karimkhani et al., "Global Skin Disease Morbidity and Mortality: An Update From Global Burden of Disease Study 2013", JAMA Dermatology, vol. 153, 2017, 7 pages.
Krauss et al., "Is the problem list in the eye of the beholder? An exploration of consistency across physicians", Journal of the American Medical Informatics Association, vol. 23, No. 5, 2016, pp. 859-865.
Liu et al., "A deep learning system for differential diagnosis of skin diseases", arXiv:1909.05382, https://arxiv.org/ftp/arxiv/papers/1909/1909.05382.pdf, 73 pages.
Lowell et al., "Dermatology in primary care: Prevalence and patient disposition, Journal of American Academy of Dermatology", vol. 45, No. 2, 2001, pp. 250-255.
Maron et al., "Systematic outperformance of 112 dermatologists in multiclass skin cancer image classification by convolutional neural networks", European Journal of Cancer, vol. 119, 2019, pp. 57-65.
Microsoft Docs, "Permutation Feature Importance", Azure Machine Learning Studio, https://docs.microsoft.com/en-us/previous-versions/azure/machine-learning/studio-module-reference/permutation-feature-importance, retrieved on May 12, 2022, 5 pages.
Mishra et al., "Interpreting Fine-Grained Dermatological Classification by Deep Learning", IEEE/CVF Conference on Computer Vision and Pattern Recognition (CVPR) Workshops, 2019, 9 pages.
Model Dermatology, https://modelderm.com/, retrieved on May 9, 2022, 1 page.
Moreno et al., "Prospective study to assess general practitioners' dermatological diagnostic skills in a referral setting", Australasian Journal of Dermatology, vol. 48, No. 2, 2007, pp. 77-82.
Okuboyejo et al., "Automating skin disease diagnosis using image classification", proceedings of the world congress on engineering and computer science, vol. 2, 2013, pp. 850-854.
Opitz et al., "Popular Ensemble Methods: An Empirical Study", Journal of Artificial Intelligence Research, vol. 11, 1999, pp. 169-198.
Ramsay et al., "Primary care in dermatology: Whose role should it be?", Journal of the American Academy of Dermatology, vol. 35, No. 6, 1996, pp. 1005-1008.
Resnick et al., "The dermatology workforce shortage, Journal of the American Academy of Dermatology", vol. 50, No. 1, 2004, pp. 50-54.
Romano et al., "Tinea incognito in Italy: a 15-year survey", Mycoses, vol. 49, 2006, pp. 383-387.
Russakovsky et al., "ImageNet Large Scale Visual Recognition Challenge", arXiv:1409.0575v3, https://arxiv.org/abs/1409.0575, 43 pages.
Seth et al., "Global Burden of Skin Disease: Inequities and Innovations", Current Dermatology Reports, 2017, pp. 204-210.

(56) References Cited

OTHER PUBLICATIONS

Simpson et al., "Will Systematized Nomenclature of Medicine-Clinical Terms improve our understanding of the disease burden posed by allergic disorders?", Clinical & Experimental Allergy, vol. 37, 2007, pp. 1586-1593.

SkinVision, https://www.skinvision.com/, retrieved on May 9, 2022, 8 pages.

Snoek et al., "Early versus Late Fusion in Semantic Video Analysis", 13th annual ACM international conference on Multimedia, 2005, pp. 399-402.

Snomed Home page, https://www.snomed.org/, retrieved on May 12, 2022, 1 page.

Sun et al., "A Benchmark for Automatic Visual Classification of Clinical Skin Disease Images", Computer Vision—ECCV 2016, Lecture Notes in Computer Science, vol. 9910, 17 pages.

Sun et al., Axiomatic Attribution for Multilinear Functions, arXiv:1102.0989v2, https://arxiv.org/abs/1102.0989, 21 pages.

Szegedy et al., "Inception-v4, Inception-ResNet and the Impact of Residual Connections on Learning", Thirty-First AAAI Conference on Artificial Intelligence, 2017, pp. 4278-4284.

Tran et al., "Assessing diagnostic skill in dermatology: A comparison between general practitioners and dermatologists", Australasian Journal of Dermatology, vol. 46, 2005, pp. 230-234.

Tschandl et al., "Comparison of the accuracy of human readers versus machine-learning algorithms for pigmented skin lesion classification: an open, web-based, international, diagnostic study", The Lancet Oncology, vol. 20, No. 7, 2019, pp. 938-947.

UpToDate, https://www.wolterskluwer.com/en/solutions/uptodate, retrieved on May 12, 2022, 9 pages.

Webber et al., "A Similarity Measure for Indefinite Rankings", ACM Transaction on Information Systems, vol. 28, No. 4, 2010, pp. 1-34.

Wilmer et al., "Most common dermatologic conditions encountered by dermatologists and nondermatologists", Cutis 94, 2014, pp. 285-292.

Yang et al., "Clinical Skin Lesion Diagnosis using Representations Inspired by Dermatologist Criteria", IEEE Conference on Computer Vision and Pattern Recognition (CVPR), 2018, pp. 1258-1266.

Yim et al., "Teledermatology in the United States: An Update in the Dynamic Era", Telemedicine and e-Health, vol. 24, No. 9, 2018, pp. 691-697.

Yuan et al., "Automatic Skin Lesion Segmentation Using Deep Fully Convolutional Networks With Jaccard Distance", IEEE Transactions on Medical Imaging, vol. 36, No. 9, 2017 pp. 1876-1886.

\* cited by examiner

DEEP LEARNING SYSTEM FOR DIFFERENTIAL DIAGNOSIS OF SKIN DISEASES

RELATED APPLICATIONS

This application claims priority under 35 U.S.C. § 371 to International Application No. PCT/US2020/050472 filed on Sep. 11, 2020, which claims priority to and the benefit of U.S. Provisional Patent Application No. 62/898,835, filed Sep. 11, 20197. Applicant claims priority to and the benefit of each of such applications and incorporates all such applications herein by reference in their entirety.

FIELD

The present disclosure relates generally to diagnostic technology. More particularly, the present disclosure relates to using deep learning models to diagnose skin diseases.

BACKGROUND

Skin disease is a leading global cause of nonfatal disease, affecting individuals in all geographies and age groups. Skin disease is also one of the most common complaints of patients seeking medical care. However, doctors with specific expertise in skin diseases (e.g., dermatologists) can be in short supply. This problem can be exacerbated in rural areas or areas with high levels of poverty. In some cases, other medical professionals, such as primary care physicians (PCPs), nurse practitioners (NPs), and physician assistants, are called upon to diagnose these conditions. Medical professionals with limited training and experience in diagnosing skin diseases can have lower accuracy when diagnosing skin diseases. Low diagnostic accuracy can lead to poor patient outcomes.

SUMMARY

Aspects and advantages of embodiments of the present disclosure will be set forth in part in the following description, or can be learned from the description, or can be learned through practice of the embodiments.

One example aspect of the present disclosure is directed to a computer-implemented method. The method includes obtaining, by a computing system, a plurality of images that respectively depict a portion of a patient's skin. The method includes determining, by the computing system using a first portion of a machine-learned skin condition classification model, a plurality of embeddings respectively for the plurality of images, the respective embedding for each image produced by a respective instantiation of the first portion of the machine-learned skin condition classification model by processing such image. The method includes combining, by the computing system, the plurality of embeddings to obtain a unified representation associated with the portion of the patient's skin. The method includes determining, by the computing system using a second portion of the machine-learned skin condition classification model, a skin condition classification for the portion of the patient's skin, the skin condition classification produced by the second portion of the machine-learned skin condition classification model by processing the unified representation, wherein the skin condition classification identifies one or more skin conditions selected from a plurality of potential skin conditions.

The method may further comprise obtaining metadata associated with the patient; determining, by the computing system using a context component of the machine-learned skin condition classification model, an additional feature representation based on the patient metadata; and generating a combination of the unified representation and the additional feature representation, wherein the skin condition classification is produced by the second portion of the machine-learned skin condition classification model by processing the combination of the unified representation and the additional feature representation. The patient metadata may include demographic data associated with the patient. The patient metadata may include medical history data associated with the patient.

The skin condition classification may comprise a differential diagnosis. The differential diagnosis may identify a plurality of potential skin conditions. Each respective potential skin condition in the plurality of potential skin conditions may include a confidence value.

A number of images included in the plurality of images may be based on a number submitted by a user. The first portion of the machine-learned skin condition classification model may be a convolutional neural network. The machine-learned skin condition classification model may be trained using a set of training data, the set of training data is produced by an aggregation process comprising: obtaining, by the computing system, unprocessed labeling data for a respective skin condition case; processing, by the computing system, the unprocessed labeling data to produce processed labeling data by matching the unprocessed labeling data with one or more skin conditions; normalizing, by the computing system, the processed labeling data; aggregating, by the computing system, normalized processed labeling data from a plurality of labelers to create aggregated label labeling data, wherein the aggregated labeling data is used in the set of training data.

Another example aspect of the present disclosure is directed to a device that includes one or more processors and a memory that stores instructions that, when executed by the one or more processors, cause the device to perform operations. The operations include obtaining, by the one or more processors, one or more images that respectively depict a portion of a user's skin. The operations include determining, by the one or more processors using a first portion of a machine-learned skin condition classification model, one or more embeddings respectively for the one or more images, the respective embedding for each image produced by a respective instantiation of the first portion of the machine-learned skin condition classification model by processing such image. The operations include obtaining, by the one or more processors, metadata associated with the user. The operations include determining, by the one or more processors and using a context component of the machine-learned skin condition classification model, an additional feature representation based on the user metadata. The operations include generating, by the one or more processors, a unified representation of the one or more embeddings and the additional feature representation. The operations include determining, by the one or more processors using a second portion of the machine-learned skin condition classification model, a skin condition classification for the portion of the user's skin, the skin condition classification produced by the second portion of the machine-learned skin condition classification model by processing the unified representation, wherein the skin condition classification identifies one or more skin conditions selected from a plurality of potential skin conditions.

The one or more images may include a plurality of images and the first portion of the machine learned classification model may determine a plurality of embeddings for the plurality of images. The operations may further comprise: combining, by the one or more processors, the plurality of embeddings to obtain a unified representation associated with the portion of the user's skin; and wherein the second portion of the machine-learned skin condition classification model determines a skin condition classification: obtaining, by the one or more processors, metadata associated with the user; determining, by the one or more processors using a context component of the machine-learned skin condition classification model, an additional feature representation based on the user metadata; and generating, by the one or more processors, a combination of the unified representation and the additional feature representation, wherein the skin condition classification is determined by the second portion of the machine-learned skin condition classification model by processing the combination of the unified representation and the additional feature representation.

The user metadata may include demographic data associated with the user. The user metadata may include medical history data associated with the user. The skin condition classification may comprise a differential diagnosis. The differential diagnosis may identify a plurality of potential skin conditions. The user metadata may be obtained from a computing device associated with a user.

Another example aspect of the present disclosure is directed to a computer-implemented method. The method includes accessing, by a computing system, historical skin condition data, the historical skin condition data including data representing a plurality of skin condition cases, each skin condition case including one or more images associated with the respective skin condition case. The method includes adding, by the computing system, one or more diagnostic labels to one or more of the plurality of skin condition cases included in the historical skin condition data. Adding one or more diagnostic labels to a respective skin condition case includes: receiving, by the computing system, a plurality of differential diagnoses from a plurality of labelers; and aggregating, by the computing system, the plurality of differential diagnoses to produce an aggregated differential diagnosis for the respective skin condition case, the aggregated differential diagnosis including two or more potential skin conditions. The method includes providing, by the computing system, the one or more images associated with at least a subset of the plurality of skin condition cases as input to a skin condition classification model, the skin condition classification model having an initial set of weight values and producing a predicted differential diagnosis for each skin condition case in the subset of the plurality of skin condition cases as output. The method includes evaluating, by the computing system, a difference between the predicted differential diagnosis produced as output of the skin condition classification model and the one or more diagnostic labels associated with the subset of the skin condition cases. The method includes adjusting, by the computing system, one or more of the initial set of weight values based on the difference between the predicted differential diagnosis produced as output of the skin condition classification model and the one or more diagnostic labels associated with the subset of the skin condition cases.

Aggregating the plurality of differential diagnoses may further comprise: for a respective potential skin condition in the two or more potential skin conditions: generating, by the computing system, a plurality of normalized confidence values for the respective potential skin condition, each respective normalized confidence value representing a confidence value from a particular labeler in the plurality of labelers; generating, by the computing system, an average confidence value for a respective potential skin condition based on the plurality of normalized confidence values for the respective potential skin condition; and generating, by the computing system, the aggregated differential diagnosis for the respective skin condition case based on the average confidence value for each potential skin condition associated with the respective skin condition case.

Other aspects of the present disclosure are directed to various systems, apparatuses, non-transitory computer-readable media, user interfaces, and electronic devices. It will be appreciated that aspects can be combined such that features described in the context of one aspect can be carried out in the context of another aspect.

These and other features, aspects, and advantages of various embodiments of the present disclosure will become better understood with reference to the following description and appended claims. The accompanying drawings, which are incorporated in and constitute a part of this specification, illustrate example embodiments of the present disclosure and, together with the description, serve to explain the related principles.

BRIEF DESCRIPTION OF THE DRAWINGS

Detailed discussion of embodiments directed to one of ordinary skill in the art is set forth in the specification, which refers to the appended figures, in which.

DETAILED DESCRIPTION

Figure 1:
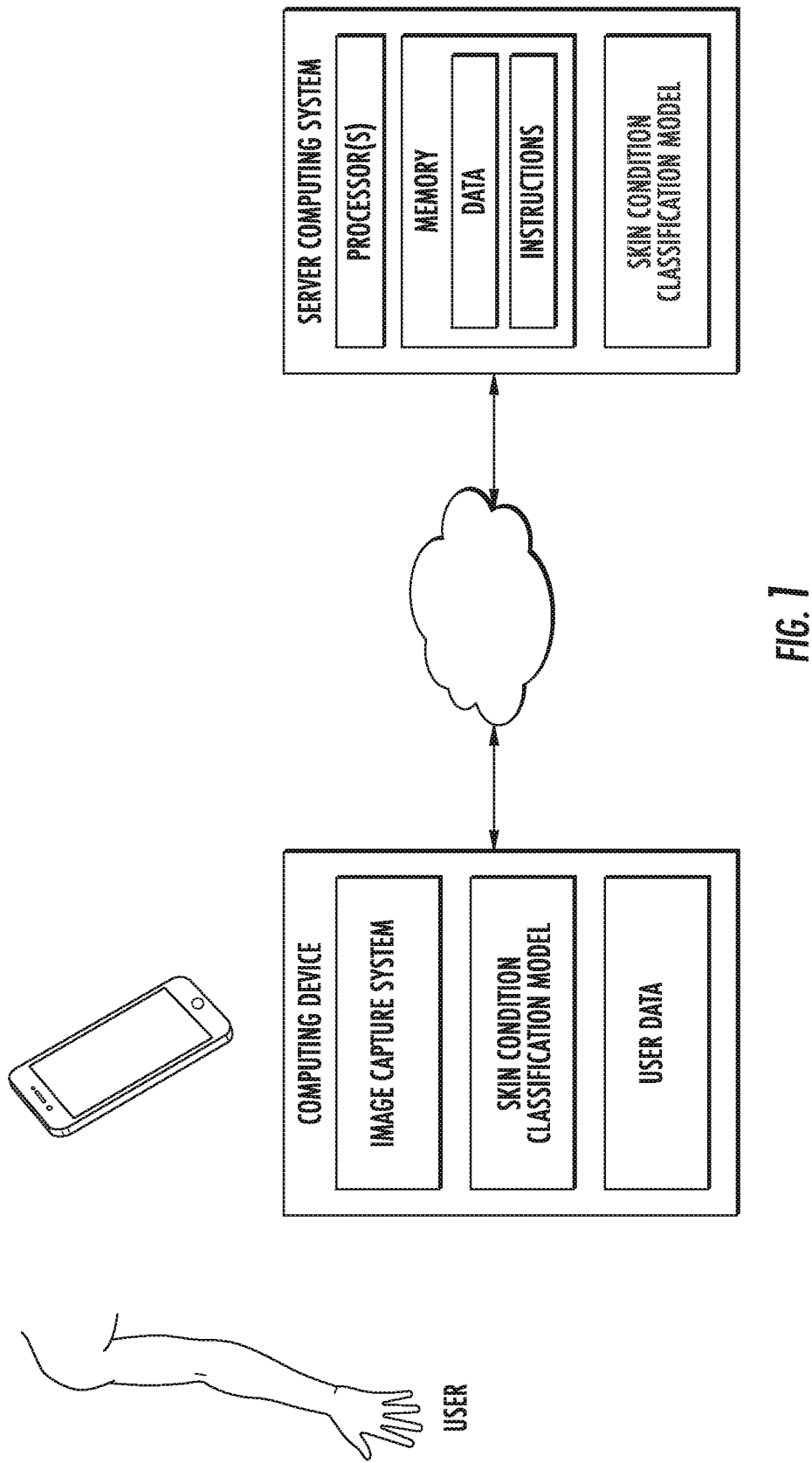
FIG. 1 depicts an example client-server environment according to example embodiments of the present disclosure.

Generally, the present disclosure is directed to systems and methods that use machine-learned models to provide differential diagnoses for skin conditions based on images with associated metadata. For example, the machine-learned models can be artificial neural networks (hereafter "neural networks"). In particular, aspects of the present disclosure allow a computing system to receive a plurality of images of a patient's skin. The computing system can use a first portion of a machine-learned skin condition classification model to generate a respective embedding for each of the plurality of images. The computing system can combine the embeddings into a unified image representation associated with the patient's skin and can use a second portion of the machine-learned skin condition classification model to generate a skin condition classification for the patient's skin based on the unified image representation. According to another aspect, in some implementations, the skin condition classification provided by the skin condition classification model can be a differential diagnosis that identifies one or more skin conditions out of a plurality of potential skin conditions. Furthermore, according to another aspect, in some implementations, metadata associated with the patient can also be additional input into the model and the machine-learned skin condition classification model can be configured to jointly process such additional patient metadata alongside the input imagery to produce the output skin condition classification. For example, the additional patient metadata can include patient demographic information, medical history, and/or other information concerning the patient.

The proposed systems and methods can be used for diagnostic and educational purposes. As one example usage, a medical professional can, as part of a diagnostic procedure, identify an area of a patient's skin that may include a skin condition. The medical professional can capture (e.g., using a camera operated by the medical professional) a plurality of images of the identified area of the patient's skin using a computing device such as a smartphone or digital camera. The captured images can be provided to a machine-learned skin condition classification model which is located locally or remotely. The machine-learned skin condition classification model can generate a skin condition classification for the identified portion of the patient's skin. The skin condition classification can include one or more potential skin conditions and a confidence value associated with each potential skin condition. The medical professional can use the skin condition classification to assist in diagnosing the patient's condition. Thus, the proposed system can serve as support role for a medical professional that is treating or examining the patient in person. The use of this system can increase the effectiveness of a medical professional while helping to reduce the time needed to diagnose a patient accurately.

As another example usage, the medical professional can be remote relative to the patient and the proposed system can facilitate a remote diagnostic examination of the patient by the medical professional, which in some cases may be referred to as "telemedicine" or "telehealth." In particular, in one example, the patient can capture (e.g., using a device belonging to the patient) one or more images of the patient's skin. The image(s) can be provided to a machine-learned skin condition classification model which is located locally or remotely. The machine-learned skin condition classification model can generate a skin condition classification and the image(s) and the skin condition classification can be provided to the medical professional that is remote from the patient. The medical professional can use the skin condition classification to assist in diagnosing the patient's condition. The diagnosis made by the medical professional can then be provided to the patient. This process can happen in real time or can occur in stages (e.g., over several hours or days). Thus, the proposed system can perform a support role for a medical professional that is treating or examining the patient via a telemedicine application or other software system. The use of this system can increase the effectiveness of a medical professional while helping to reduce the time and expense needed to diagnose a patient accurately (e.g., the patient can receive improved diagnostic care without needing to visit the medical professional in person). In some implementations, the telemedicine experience can occur through a dedicated application which may, for example, facilitate a patient in choosing from among multiple different potential providers and/or facilitate video conferencing between the patient and the medical professional. For example, the dedicated application can include a list of providers of medical services. As such, if a patient receives a differential diagnosis through the dedicated application, the dedicated application can also provide information on which, if any, service providers may best provide future medical services (e.g., if a given skin condition is determined to likely be cancerous, the dedicated application can recommend a medical professional who specializes in skin cancer).

As yet another example usage, the machine learning systems described herein can enable improved patient education and/or provide an initial automated screening in which a patient is given an initial computer-based screening and recommendation regarding seeking further medical care. For example, a patient can capture (e.g., using a device belonging to the patient) one or more images of the patient's skin. The image(s) can be provided to a machine-learned skin condition classification model which is located locally or remotely. The machine-learned skin condition classification model can generate a skin condition classification. Based on the skin condition classification, the patient can be provided with additional information regarding potential skin conditions (e.g., the conditions predicted by the model) and/or can be provided with a recommendation regarding whether, when, how, and/or with whom to seek additional medical care.

Further to the descriptions above, a patient may be provided with controls allowing the patient to make an election as to both if and when systems, programs, or features described herein may enable collection of patient information (e.g., images of a patient, patient metadata such as patient demographics and medical history, etc.), with whom such patient information (or information derived or predicted therefrom) is shared, and how such patient information (or information derived or predicted therefrom) is used to improve the product moving forward.

In addition, certain data may be treated in one or more ways before it is stored or used, so that personally identifiable information is removed. For example, a patient's identity may be processed so that no personally identifiable information can be determined for the patient, or a patient's geographic location may be generalized where location information is obtained (such as to a city, ZIP code, or state level), so that a particular location of a patient cannot be determined. Thus, the patient has control over what information is collected about the patient, how that information is used, and what information is provided to the patient.

Further, the data used by any of the systems or models described herein (e.g., for training and/or inference) can be de-identified data. For example, personally identifiable information, such as location, name, exact birth date, contact information, biometric information, facial photographs, etc. can be scrubbed from the data prior to being transmitted to and/or utilized by the models and/or a computing system including the models. For example, the data can be de-identified to protect identity of individuals and to conform to regulations regarding medical data, such as HIPAA, such that no personally identifiable information (e.g., protected health information) is present in the data used by the models and/or used to train the models.

Example implementations of the present disclosure can assist in diagnosing skin diseases. However, such example implementations are not necessarily a substitute for medical expertise and proper medical treatment, but instead may provide an estimation as a tool for qualified medical personnel to make informed decisions or to enable a user to seek more information.

Thus, the systems and methods of the present disclosure provide improved techniques to diagnose skin diseases using a machine-learned model. More particularly, a diagnostic system can obtain, or receive, a plurality of images of a portion of a patient's skin. The number of images included in the plurality of images is flexible and depends on the number of images submitted by a user or medical professional. The diagnostic system can pass the plurality of images to a machine-learned skin condition classification model. In some examples, the machine-learned skin condition classification model includes two or more portions, each portion trained to perform a particular step in the process of identifying skin conditions. For example, a first portion of the machine-learned skin condition classification model which can in some instances be referred to as an "image embedding model" or "feature extraction model" can be trained to process images that depict a portion of a patient's (or user's) skin.

The diagnostic system can, using the first portion of the machine-learned skin condition classification model, determine a plurality of embeddings respectively for the plurality of obtained images. Each image can be processed by a particular instantiation of the first portion of the machine-learned skin condition classification model. In some implementations, all images can be processed concurrently (e.g., in parallel) without delay. The embedding produced for each image can be a representation of the image in a low-dimensional dense vector form, such that the important data in the image is extracted and represented in a form that is less sparse and is more efficient for calculation, storage, and transmission. The plurality of embeddings can be combined to generate a unified image representation. For example, the unified image representation can be generated by averaging the embedding values for a plurality of embeddings.

In addition, in some implementations, the diagnostic system can access patient metadata. Patient metadata can include a patient's demographic data, including but not limited to, age, height, weight, and so on. Patient metadata can include a patient's clinical medical data, including but not limited to a patient's reported symptoms, a patient's answers to relevant medical questions, a medical professional's observations, and so on. The patient metadata can include a patient's medical history, including but not limited to, past medical procedures, past diagnoses, allergies, family medical history, and so on. In some examples, the patient metadata can be analyzed by a context component of the machine-learned skin condition classification model. The context component can generate a metadata feature representation of the patient metadata. As described above, the patient can be provided with controls allowing the patient to make an election as to both if and when systems, programs, or features described herein may enable collection, storage, and/or use the patient information described above.

In some examples, the diagnostic system can generate a combination of the unified image representation of images and the metadata feature representation of the patient metadata. For example, the feature representation can be concatenated with the unified image representation. Once the image embeddings have been combined (e.g., averaged) to form a unified image representation and the feature representation of the patient metadata has been integrated (e.g., concatenated) to form an integrated representation, the diagnostic system can use a second portion of the machine-learned skin condition classification model which can in some instances be referred to as a "differential diagnosis model" or "classification head" to determine a skin condition classification based on the integrated representation.

In some implementations, the skin condition classification can be a differential diagnosis. Differential diagnoses can identify or select one or more skin conditions from a plurality of potential skin conditions. In some instances, the model can also output a confidence level associated with each identified skin condition. The confidence level for a particular potential skin condition can represent the likelihood that the portion of the patient's skin included in the received images is afflicted with the corresponding skin condition. The higher the confidence level associated with a respective potential skin condition, the higher the likelihood that the respective condition is actually present.

Once a skin condition classification has been generated, the diagnostic system can provide the skin condition classification to a medical professional to assist in a medical professional's diagnostic process. In other examples, a user can access the diagnostic system as an educational tool (e.g., provide information on skin conditions) to help the user. For example, a user may be unsure of what symptoms or presentation may be associated with a particular skin condition and may use images to help identify whether to seek medical help and/or treatment.

The diagnostic system can generate and train the machine-learned skin condition classification model before performing any skin condition classifications. To train the machine-learned skin condition classification model, the diagnostic system can obtain historical skin condition data. The historical skin condition data can include a plurality of distinct skin condition cases. A skin condition case represents data associated with a particular instance of a patient being diagnosed for a potential skin condition. The data associated with a particular skin condition case can include images of the affected skin area, case history, patient metadata, and any other data relevant to a diagnosis (e.g., location of the patient, year of diagnosis, and so on).

Once the historical skin condition data has been obtained, the diagnostic system can obtain label data for each skin condition case in the plurality of skin condition cases. Label data can include data supplied by one or more labelers (e.g., medical professionals with experience diagnosing skin conditions). Each labeler can review the images, case history, and patient metadata to determine a differential diagnosis for the skin condition case. In some implementations, the differential diagnosis provided by each labeler is provided as a string of text and can include one or more potential skin conditions and a confidence level or ranking for each. Once a plurality of labelers have supplied unprocessed label data, the diagnostic system can process the unprocessed label data. For example, the diagnostic system can map the data provided by the labelers as text to one skin condition in a predetermined set of skin conditions stored in a skin condition database at the diagnostic system.

The diagnostic system can standardize and/or normalize the labeling data received from the plurality of labelers. For example, for a given case, if a first labeler supplies confidence values ranging from one to five and the second labeler supplies confidence values ranging from one to three, the diagnostic system can scale all values in both sets to a value between zero and one. Once the labeling data has been normalized, the diagnostic system can aggregate confidence data for each skin condition case. In some examples, aggregation can include adding the (normalized) confidence values from different labelers for each potential skin condition. The skin conditions can then be sorted into one or more classification groupings (or buckets based on the aggregated confidence scores. The bucketed skin conditions can be used as ground truth data for training the model.

As part of the training process, the diagnostic system can provide the plurality of images and patient data associated with at least a subset of the plurality of skin condition cases as input to a skin condition classification model. The skin condition classification model can include an initial set of weight values. The skin condition classification model can produce an estimated differential diagnosis for each skin condition case. The diagnostic system can compare (e.g., using an objective function or loss function) the estimated differential diagnosis for a skin condition case with the ground truth labeling data for that skin condition case. Based on the comparison, the diagnostic system can adjust the weight values in an attempt to produce a closer match between the estimated differential diagnosis and the labeling data. For example, a gradient of the loss function can be backpropagated through the model to determine updates to the weight values of the model that reduce the loss function. In some implementations, the skin condition classification model can be trained end-to-end. In other implementations, individual portions of the model can be separately trained or pre-trained on various forms of data. For example, the image embedding portion of the skin condition classification model can be pre-trained on standard image classification data (e.g., images that are not specifically related to skin conditions).

In more detail, the diagnostic system can access historical skin condition case data. The historical skin condition case data can include one or more images of an affected area, user medical data, and user demographic table. The data preparation system can obtain raw diagnosis entries from one or more labelers. The one or more labelers can be medical professionals such as doctors (e.g., dermatologists), nurse practitioners, and so on.

The raw diagnosis entries can include text strings entered by the labelers. The data preparation system can map the raw diagnostic entries to a defined set of skin conditions. Thus, each skin condition case can have one or more mapped conditions from each labeler. In some examples, the data preparation system can associate one or more confidence values with each mapped skin condition from each labeler. As seen in this example, each labeler generated a diagnosis with at least two possible skin conditions, each possible skin condition having an associated likelihood value or confidence value (e.g., which may be formatted as a relative ranking).

The data preparation system can reweight or normalize the mapped conditions data such that each confidence value is a score between zero and one. The data preparation system can aggregate confidence values across labelers by, for example, adding the confidence values for each potential skin condition together from the confidence values associated with each labeler. For example, if a first labeler listed acne with the competence of 0.5 and the second labeler listed of acne with the confidence of 0.1, the aggregated value could be 0.6.

The data preparation system can group the potential skin conditions into one or more buckets. For example, the skin conditions can be grouped into three classification groups: skin conditions with a high aggregated confidence score, skin conditions with a medium confidence score, and skin conditions with a low aggregated confidence store. Once the skin conditions have been grouped into one or more classification groups, the skin condition data can be used as ground truth data for use while training a machine-learned skin condition classification model. The classification group assignment process can be based on application of confidence thresholds or can be performed as a relative ranking. In other examples, the potential skin conditions are not sorted into classification groups. Instead, the potential skin conditions are ordered from most likely (based on confidence score) to least likely but not grouped.

In some implementations, an entirety of the skin condition classification model is stored and implemented at a single device (e.g., the patient's device, the medical professional's device, a server device, etc.). In other implementations, some portions of the skin condition classification model (e.g., the image embedding portion and/or the context component) can be stored and implemented at a first device (e.g., the patient's device or the medical professional's device) while other portions of the skin condition classification model (e.g., the differential diagnosis portion) can be stored and implemented at a second device (e.g., a server device). In such fashion, certain data such as patient images and/or patient metadata may never leave the local device (e.g., the patient's device). Instead, only an uninterpretable embedding or representation is transmitted from the local device to the server device. This arrangement can improve patient privacy.

The systems and methods described herein provide a number of technical effects and benefits. More particularly, the systems and methods of the present disclosure provide improved techniques for providing a differential diagnosis of skin conditions based on images of the affected skin area using a machine-learned skin condition classification model. For instance, the machine-learned skin condition classification model (and its associated processes) allow both medical professionals and users to access additional information (both diagnostic and educational) about one or more skin conditions quickly and efficiently, saving time, money, and reducing the need for more expensive and inconvenient tests. In addition, the information provided by the machine-learned skin condition classification model can improve the accuracy of diagnoses and patient outcomes. As such, the disclosed system can significantly reduce the cost and time needed to provide diagnostic information.

FIG. 1 depicts an example client-server environment according to example embodiments of the present disclosure. Specifically, FIG. 1 depicts a user computing device and a server system that communicate over a network. The computing device can be a personal electronic device such as a smartphone, tablet, and so on. The computing device can include an image capture system, at least a portion of a skin condition classification model, and user data. The image capture system can capture one or more images of a user's skin (e.g., the depicted arm). The skin condition classification model can include at least a portion of the skin condition classification model that generates embeddings for one or more images. In this way, the computing device can transmit an embedding representing the image, rather than the image itself. This can reduce the amount of bandwidth needed to transmit the images to the server computing system.

The user data can be stored in a local data storage device and can include user clinical data, user demographic data, and user medical history data. This information can be transmitted to the server computing system as needed with user permission. In some examples, the skin condition classification model at the user computing device can include a context component that generates a feature representation for the user data. In some examples, the skin condition classification model can combine one or more image embeddings and the feature representation data for the user data.

The server computing system includes one or more portions of a skin condition classification model. For example, the server computing system can receive one or more of: image data, one or more embeddings, a unified image representation of multiple embeddings, a feature representation of user data, or a combined representation of unified image representations and a feature representation. Any and/or all of these types of data can be received at the server computing system and used to generate one or more skin condition classifications. The skin condition classifications can be transmitted to the computing device or to another third-party device as needed.

Figure 2A:
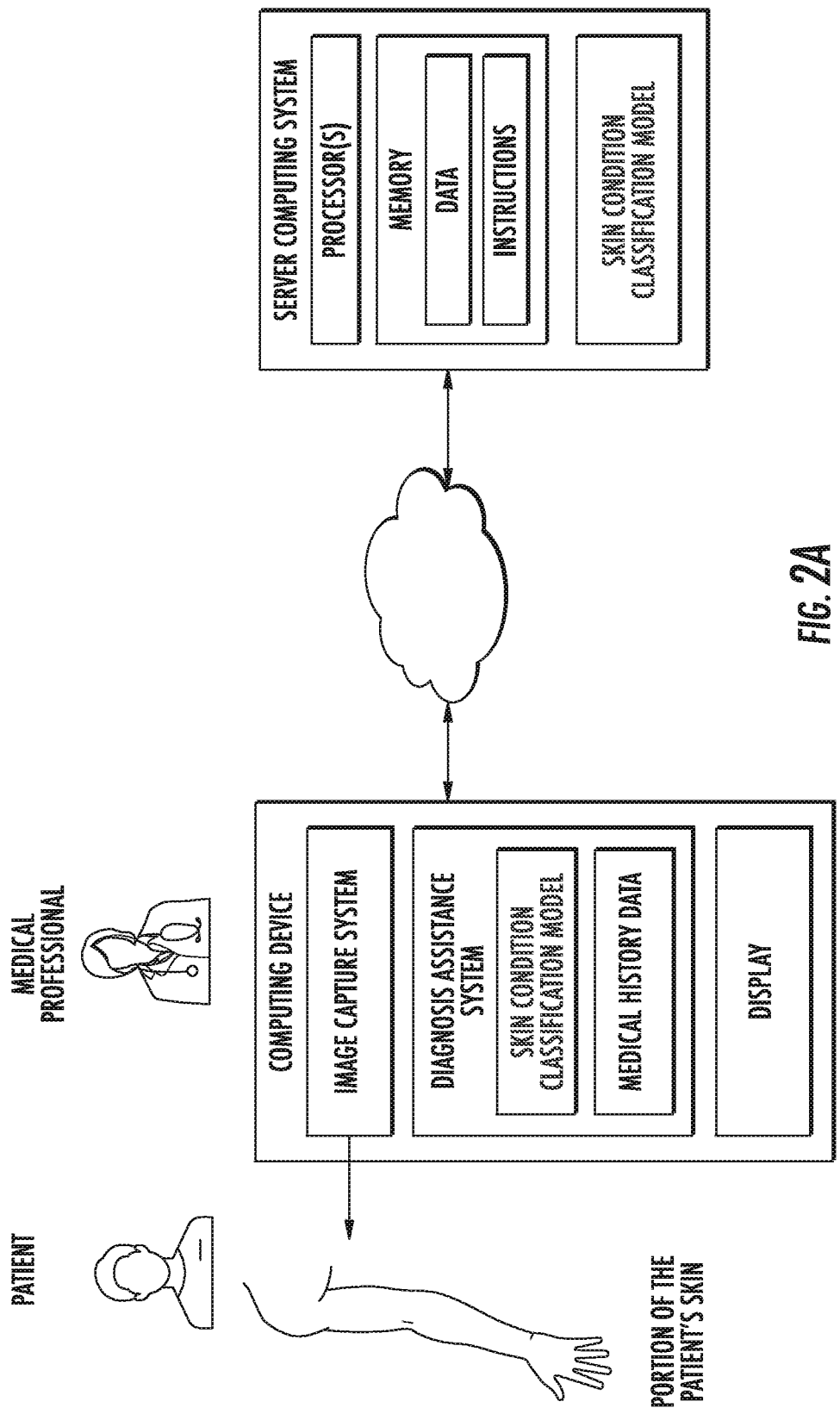
FIG. 2A depicts an example block diagram of a system for providing diagnosis assistance according to example embodiments of the present disclosure.

FIG. 2A depicts an example block diagram of a system for providing diagnosis assistance according to example embodiments of the present disclosure. In this example, the computing device is associated with a medical professional (e.g., a doctor, a nurse practitioner, and so on). The medical professional can utilize the computing device to obtain aid during their diagnostic process. The computing device can include an image capture system (e.g., a camera and associated software), a diagnosis assistance system, and a display. The diagnosis assistance system can include one or more portions of a skin condition classification model and medical history data.

The medical professional can use the computing device to capture one or more images of a patient's skin using the image capture system. The diagnosis assistance system can either generate embeddings locally or transmit the raw image data to the server computing system. Similarly, medical history data can be processed locally to generate a feature representation or transmitted to the server computing system. In some examples, the diagnosis assistance system includes the full skin condition classification model and thus can generate skin condition classifications without transmitting data to the server computing system.

In some examples, the diagnostic assistance system transmits data to the server computing system. The skin condition classification model at the server computing system can generate one or more skin condition classifications and transmit the data back to the diagnosis assistance system for display to the medical professional in the display at the computing device.

Figure 2B:
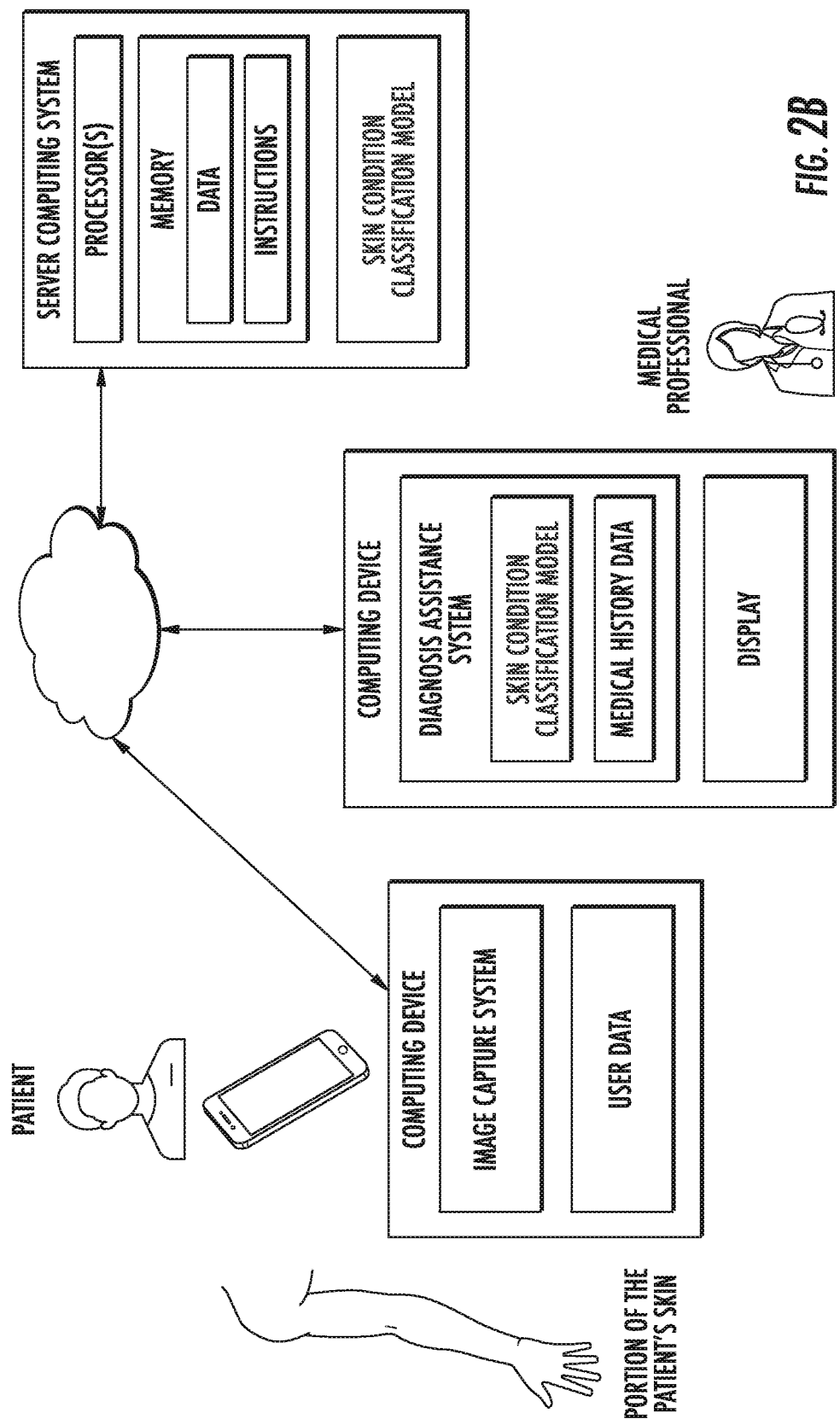
FIG. 2B depicts an example block diagram of a system for providing diagnosis assistance according to example embodiments of the present disclosure.

FIG. 2B depicts an example block diagram of a system for providing diagnosis assistance according to example embodiments of the present disclosure. In this example, the patient is not physically present with the medical professional. Instead, the patient uses a computing device with an image capture system to transmit one or more images (and potentially user data) to the computing device associated with the medical professional via a network. Once the computing device receives the one or more images from the computing device associated with the patient, the process can proceed as described above with respect to FIG. 2A. The medical profession can then transmit any relevant diagnostic information to the computing device of the patient.

Figure 3:
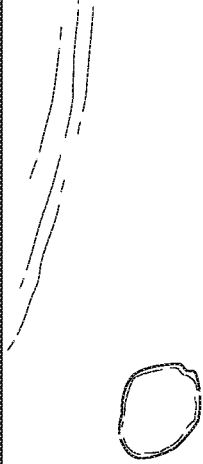
FIG. 3 depicts an example user interface according to example embodiments of the present disclosure.

FIG. 3 depicts an example user interface according to example embodiments of the present disclosure. This user interface can be for a diagnostic assistance system for use by a medical professional. The user interface can include patient data associated with the patient's case. Patient data can include one or more images of an affected skin area. The patient data can also include clinical data including, but not limited to, the patients' self-reported condition, one or more symptoms, duration of symptoms, any currently prescribed drugs, medical history and so on. This data can be presented for a medical professional to view.

The user interface can include differential diagnosis data generated by the machine-learned skin condition classification model. For example, the user interface can include an area that includes one or more potential skin conditions. Each skin condition includes a name, a confidence level, one or more clinical details (e.g., symptoms and presentation data), images of the skin condition, and the option to find more information. In some examples, the potential skin conditions are ordered based on the likelihood (as determined by the skin condition classification model) of the potential skin condition existing in the patient.

Figure 4:
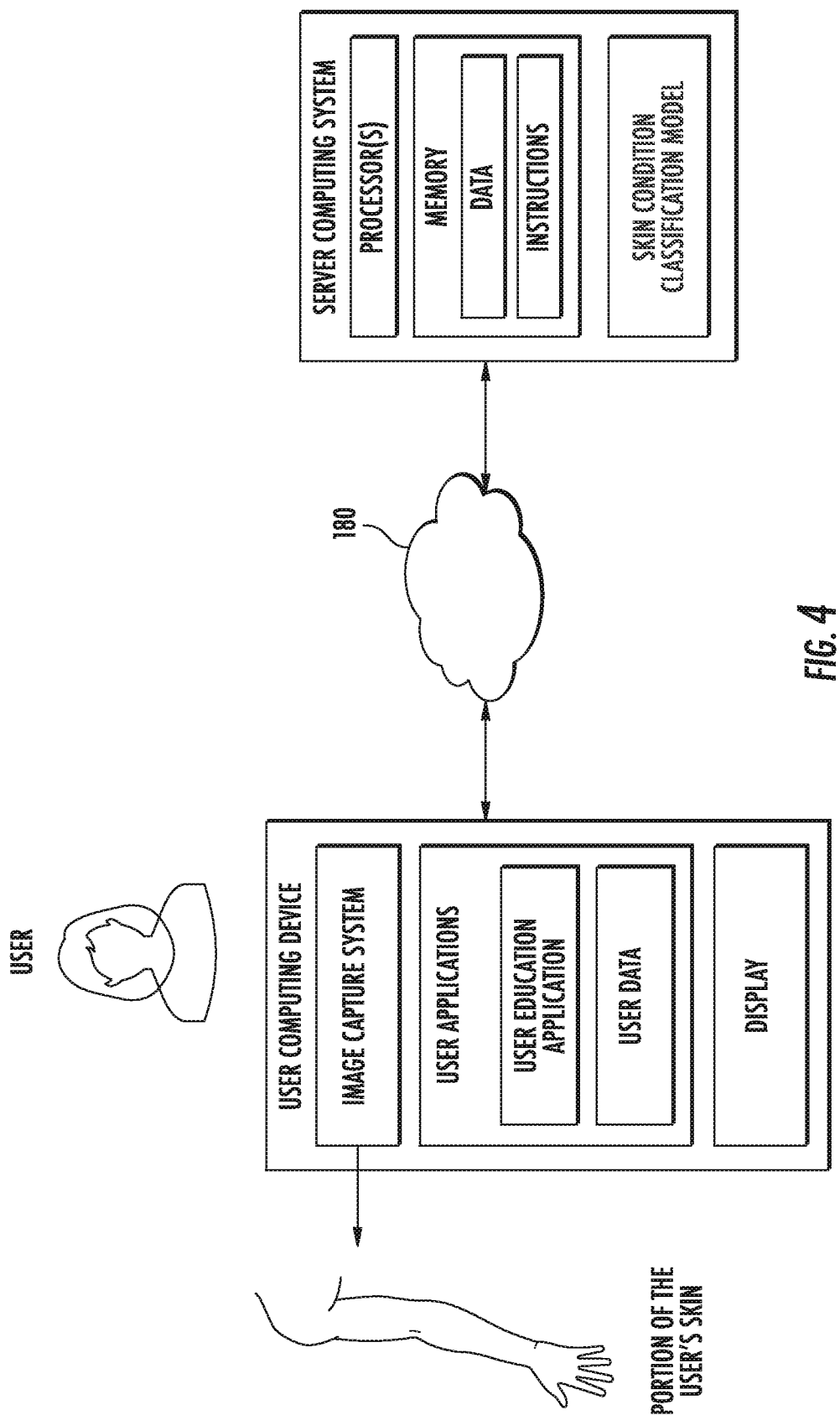
FIG. 4 depicts an example block diagram of a system for providing health care information according to example embodiments of the present disclosure.

FIG. 4 depicts an example block diagram of a system for providing health care information according to example embodiments of the present disclosure. In this example, a user seeks additional information or educational data for one or more skin conditions. The user computing device in this example can include an image capture system (e.g., a camera), one or more user applications, and a display.

The user applications can include a user education application and an application for accessing user data. The user education application can include a web browser that allows the user to access educational websites over a network. Thus, a user can use a web browser to access a skin condition classification model at a server computing system through a website. The user computing device can transmit image data to the skin condition classification model. The skin condition classification model can generate a skin condition classification and provide skin condition classification data to the user through the user education application for display.

Figure 5:
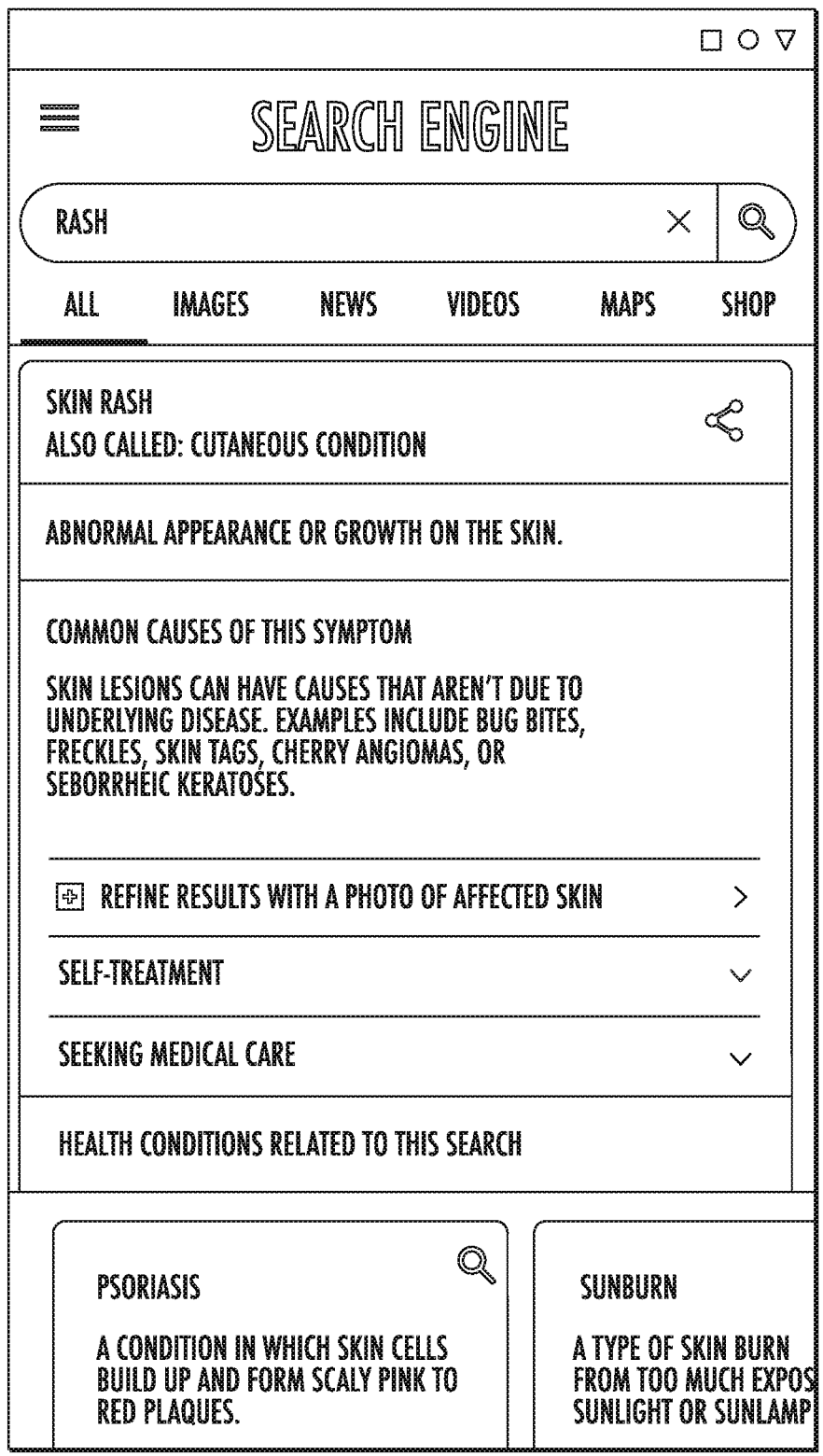
FIG. 5 depicts an example user interface according to example embodiments of the present disclosure.

FIG. 5 depicts an example user interface according to example embodiments of the present disclosure. In this example, the user interface shows a search engine (accessible through a web browser) in which a user has searched for a term associated with one or more skin conditions (e.g., a rash). In addition to providing base information about the search topic, the search engine interface can offer the user the ability to refine results with an image of a skin area that is potentially affected by the skin condition.

Figure 6:
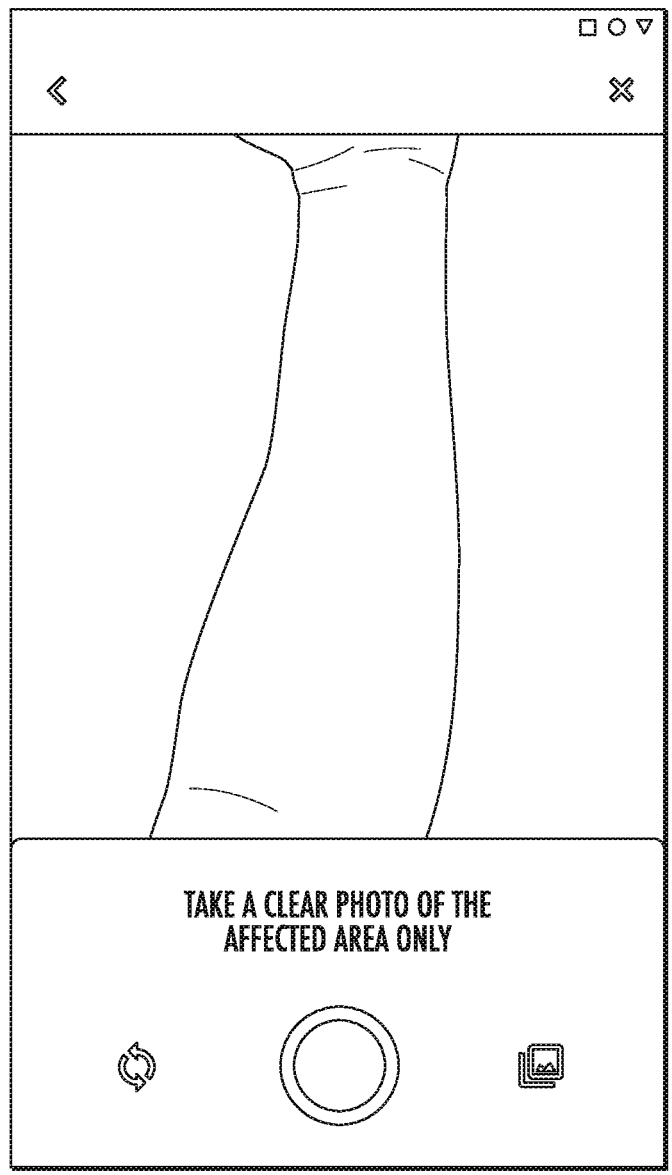
FIG. 6 depicts an example user interface according to example embodiments of the present disclosure.

FIG. 6 depicts an example user interface according to example embodiments of the present disclosure. For example, the user interface includes an interface for capturing an image of a portion of a user's skin. The user interface can include instructions for capturing appropriate images of a portion of the user's skin. The user can then capture the image and transmit it, through an application, to a server computing system.

Figure 7:
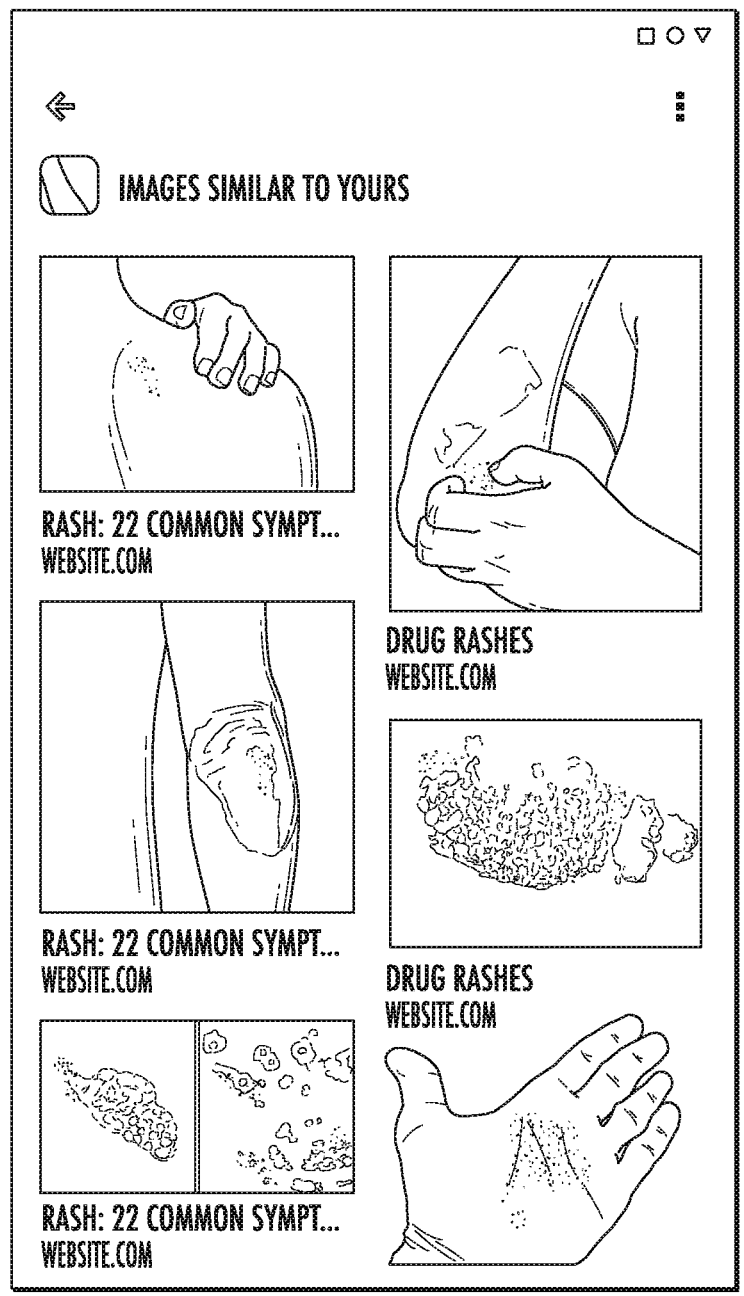
FIG. 7 depicts an example user interface according to example embodiments of the present disclosure.

FIG. 7 depicts an example user interface according to example embodiments of the present disclosure. In this example, the user interface displays one or more images that are deemed (by a machine learning trained skin condition classification model) to be similar to the images that were captured by the user device.

Figure 8:
FIG. 8 depicts a block diagram of a skin condition classification model according to example embodiments of the present disclosure.

FIG. 8 depicts a block diagram of a skin condition classification model according to example embodiments of the present disclosure. In some implementations, the skin conditional model is trained to receive a set of input data (e.g. images and user metadata) descriptive of a user with a potential skin condition, and, as a result of receipt of the input data, provide output data that represents a differential diagnosis. Thus, in some implementations, the skin condition classification model is operable to provide a differential diagnosis for a patient based on a plurality of images of the affected skin area.

A differential diagnosis can include one or more skin conditions or diseases. Each skin condition can have an associated confidence value or likelihood value that represents the probability the affected skin area is afflicted with the skin condition. In some examples, the skin condition classification model can have a predetermined selection of possible skin conditions. For example, potential skin conditions can include, but are not limited to, acne, actinic keratosis, allergic contact dermatitis, alopecia areata, basal cell carcinoma, cyst, eczema, folliculitis, hidradenitis, lentigo, melanocytic nevus, post inflammatory hyperpigmentation, psoriasis, squamous cell carcinoma or squamous cell carcinoma in situ (shown as "scc/sccis" in certain Figures for simplicity), seborrheic keratosis (shown as "sk/isk" in certain Figures for simplicity), scar condition, seborrheic dermatitis, skin tag, stasis dermatitis, tinea, tinea *versicolor*, urticaria, verruca vulgaris, vitiligo, and other.

As examples, the skin condition classification model can be or can otherwise include various machine-learned models such as neural networks (e.g., deep neural networks) or other types of machine-learned models, including non-linear models and/or linear models. Neural networks can include feed-forward neural networks, recurrent neural networks (e.g., long short-term memory recurrent neural networks), convolutional neural networks or other forms of neural networks.

One or more skin condition classification models can be stored and implemented at a user computing device and/or one or more skin condition classification models can be stored and implemented at the server computing system.

The skin condition classification model can be trained based on training data using various training or learning techniques, such as, for example, backwards propagation of errors. For example, a loss function can be backpropagated through the model(s) to update one or more parameters of the model(s) (e.g., based on a gradient of the loss function). Various loss functions can be used such as mean squared error, likelihood loss, cross entropy loss, hinge loss, and/or various other loss functions. Gradient descent techniques can be used to iteratively update the parameters over a number of training iterations. In some implementations, performing backwards propagation of errors can include performing truncated backpropagation through time. Generalization techniques (e.g., weight decays, dropouts, etc.) can be performed to improve the generalization capability of the models being trained.

In some implementations, to help the skin condition classification model learn to predict a differential diagnosis (e.g., as opposed to a pure classification to predict a single label), the target label of the skin condition classification model can be based on each case's reference standard differential diagnosis. Specifically, in some implementations, the summed confidence of each condition in the differential can be normalized (e.g., to sum to 1), and these "soft weights" can be used as the target labels, and the skin condition classification model can be trained using a softmax cross-entropy loss. To account for class imbalance, each input case can be weighted based on the inverse of the frequency of the primary diagnosis, so that cases of rare conditions contribute more to the loss function. The model weights can be optimized using a distributed stochastic gradient descent implementation.

In some implementations, an ensemble of skin condition classification models can be used according to an ensemble approach. For example, each respective skin condition classification model in the ensemble can make a respective prediction. A final prediction of the ensemble can be an aggregate (e.g., average) of the predictions from the multiple different models of the ensemble. In some implementations, each model in the ensemble is trained in the same manner.

Figure 9:
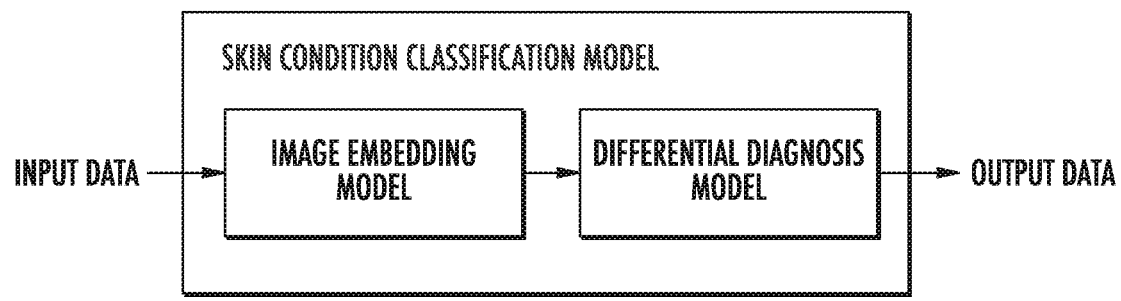
FIG. 9 depicts a block diagram of multi-step model for generating skin condition classifications based on image data according to example embodiments of the present disclosure.

FIG. 9 depicts a block diagram of multi-step model for generating skin condition classifications based on image data according to example embodiments of the present disclosure. The skin condition classification model is similar to the model depicted in FIG. 9 except that the model includes an image embedding model and a differential diagnosis model.

The image embedding model can produce a respective embedding based on each of one or more input images. The embedding can be invariant based on angle and lighting. In some examples, the embedding for each input image is a lower dimensional representation of the data in the image. The differential diagnosis model can generate a differential diagnosis based on the one or more embeddings generated by the image embedding model.

Figure 10:
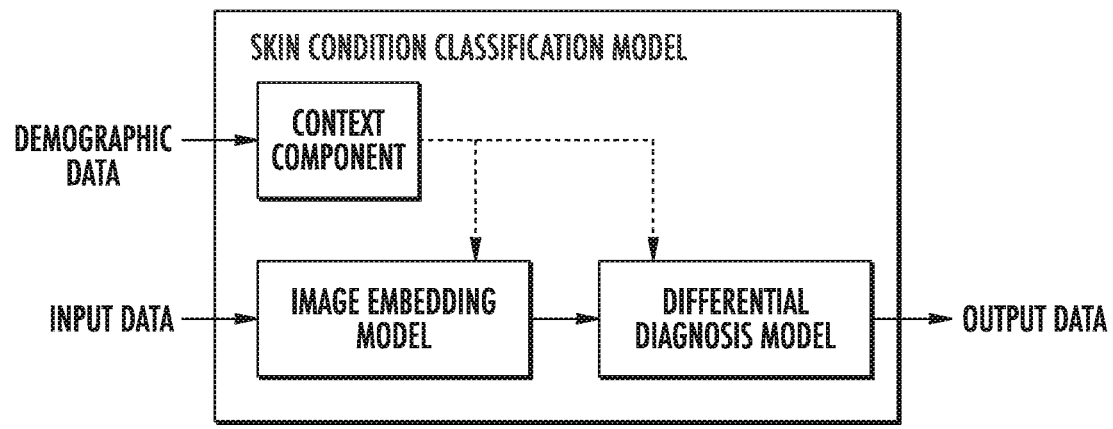
FIG. 10 depicts a block diagram of supplemented multi-step model for generating skin condition classifications based on image data according to example embodiments of the present disclosure.

FIG. 10 depicts a block diagram of supplemented multi-step model for generating skin condition classifications based on image data according to example embodiments of the present disclosure. This model is similar to the skin condition classification model shown in FIG. 9 and FIG. 10 except that it includes a context component that informs the image embedding model and the differential diagnosis model with a feature representation based on user demographic data.

Figure 11:
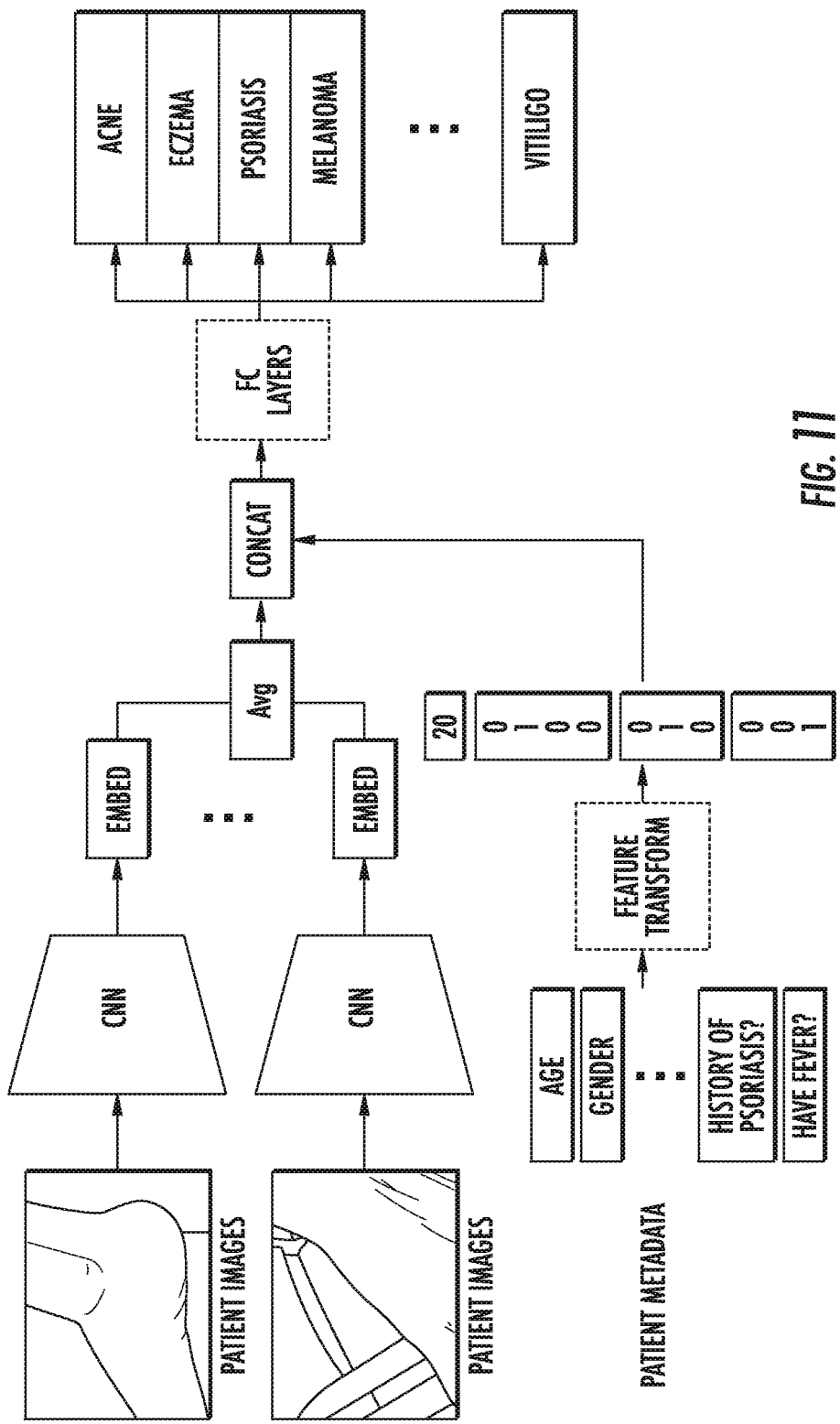
FIG. 11 depicts a block diagram of a system for generating skin condition classifications based on image data according to example embodiments of the present disclosure.

FIG. 11 depicts a block diagram of a system for generating skin condition classifications based on image data according to example embodiments of the present disclosure. The skin condition classification model can accept a plurality of images as input. Each patient image can be processed by an instantiation of a convolutional neural network (CNN) (e.g., that is a component of the skin condition classification model). Each convolutional neural network produces an embedding representation (EMBED) of a respective image. The plurality of embeddings can, for example, be averaged to produce a combined embedding representation.

The skin condition classification model can also receive patient metadata as input, including but not limited to demographic data (e.g., age and gender) and clinical data (symptoms and history). The patient metadata can be processed by a feature transform to generate a feature representation of the patient metadata. The feature representation can be concatenated with the combined feature representation into an aggregated unified image representation of patient data and the images. The skin condition classification model can use the aggregated unified image representation to generate a differential diagnosis. The differential diagnosis can include a plurality of skin conditions, each with a specific confidence value.

Figure 12:
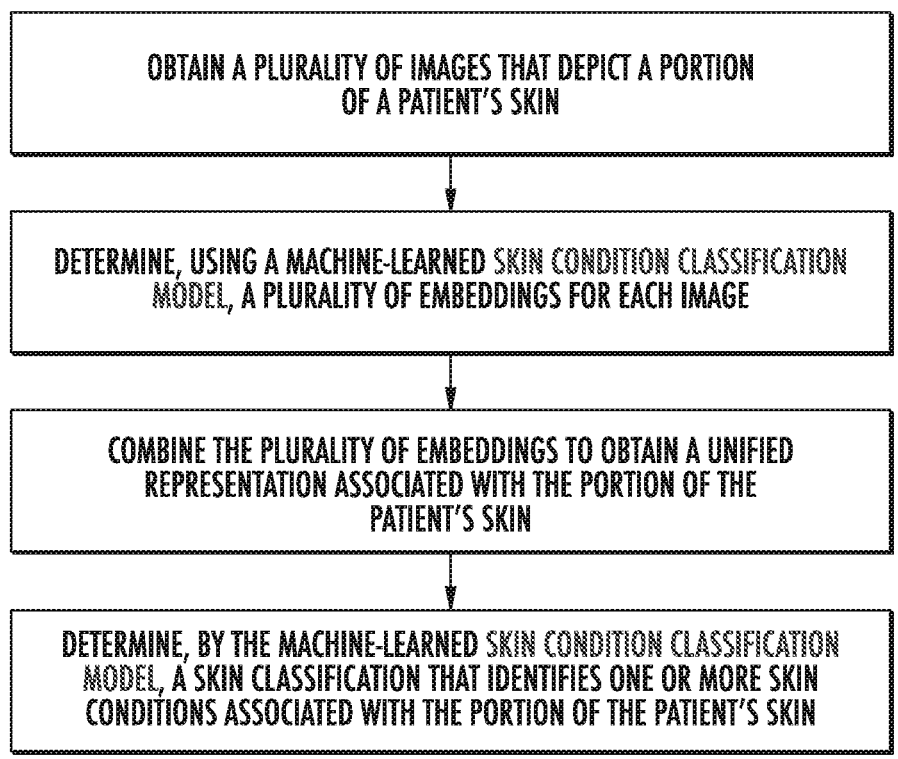
FIG. 12 depicts a flow chart of an example method for generating skin condition classifications based on image data according to example embodiments of the present disclosure.

FIG. 12 depicts a flow chart of an example method for generating skin condition classifications based on image data according to example embodiments of the present disclosure. To perform the method, a diagnostic system obtains a plurality of images that respectively depict a portion of a patient's skin.

The diagnostic system determines, using a first portion of a machine-learned skin condition classification model, a plurality of embeddings respectively for the plurality of images. The respective embedding for each image produced by a respective instantiation of the first portion of the machine-learned skin condition classification model by processing such image. The diagnostic system combines the plurality of embeddings to obtain a unified image representation associated with the portion of the patient's skin.

The diagnostic system determines using a second portion of the machine-learned skin condition classification model, a skin condition classification for the portion of the patient's skin, the skin condition classification produced by the second portion of the machine-learned skin condition classification model by processing the unified image representation, wherein the skin condition classification identifies one or more skin conditions selected from a plurality of potential skin conditions.

While the present subject matter has been described in detail with respect to various specific example embodiments thereof, each example is provided by way of explanation, not limitation of the disclosure. Those skilled in the art, upon attaining an understanding of the foregoing, can readily produce alterations to, variations of, and/or equivalents to such embodiments. Accordingly, the subject disclosure does not preclude inclusion of such modifications, variations, and/or additions to the present subject matter as would be readily apparent to one of ordinary skill in the art. For instance, features illustrated and/or described as part of one embodiment can be used with another embodiment to yield a still further embodiment. Thus, it is intended that the present disclosure cover such alterations, variations, and/or equivalents.

What is claimed is:

1. A computer-implemented method comprising:
    obtaining, by a computing system, a plurality of images that respectively depict a portion of a patient's skin;
    determining, by the computing system using a first portion of a machine-learned skin condition classification model, a plurality of embeddings respectively for the plurality of images, the respective embedding for each image produced by a respective instantiation of the first portion of the machine-learned skin condition classification model by processing such image;
    combining, by the computing system, the plurality of embeddings to obtain a unified representation associated with the portion of the patient's skin; and
    determining, by the computing system using a second portion of the machine-learned skin condition classification model, a skin condition classification for the portion of the patient's skin, the skin condition classification produced by the second portion of the machine-learned skin condition classification model by processing the unified representation, wherein the skin condition classification identifies one or more skin conditions selected from a plurality of potential skin conditions.

2. The computer-implemented method of claim 1, further comprising:
    obtaining metadata associated with the patient;
    determining, by the computing system using a context component of the machine-learned skin condition classification model, an additional feature representation based on the patient metadata; and
    generating a combination of the unified representation and the additional feature representation, wherein the skin condition classification is produced by the second portion of the machine-learned skin condition classification model by processing the combination of the unified representation and the additional feature representation.

3. The computer-implemented method of claim 2, wherein the patient metadata includes demographic data associated with the patient.

4. The computer-implemented method of claim 2, wherein the patient metadata includes medical history data associated with the patient.

5. The computer-implemented method of claim 1, wherein the skin condition classification comprises a differential diagnosis.

6. The computer-implemented method of claim 5, wherein the differential diagnosis identifies a plurality of potential skin conditions.

7. The computer-implemented method of claim 6, wherein each respective potential skin condition in the plurality of potential skin conditions include a confidence value.

8. The computer-implemented method of claim 1, wherein a number of images included in the plurality of images is based on a number submitted by a user.

9. The computer-implemented method of claim 1, wherein the first portion of the machine-learned skin condition classification model is a convolutional neural network.

10. The computer-implemented method of claim 1, wherein the machine-learned skin condition classification model is trained using a set of training data, the set of training data is produced by an aggregation process comprising:
    obtaining, by the computing system, unprocessed labeling data for a respective skin condition case;
    processing, by the computing system, the unprocessed labeling data to produce processed labeling data by matching the unprocessed labeling data with one or more skin conditions;
    normalizing, by the computing system, the processed labeling data;
    aggregating, by the computing system, normalized processed labeling data from a plurality of labelers to create aggregated label labeling data, wherein the aggregated labeling data is used in the set of training data.

11. A device comprising:
one or more processors;
a memory that stores instructions that, when executed by the one or more processors, cause the device to perform operations, the operations comprising:
    obtaining, by the one or more processors, one or more images that respectively depict a portion of a user's skin;
    determining, by the one or more processors using a first portion of a machine-learned skin condition classification model, one or more embeddings respectively for the one or more images, the respective embedding for each image produced by a respective instantiation of the first portion of the machine-learned skin condition classification model by processing such image;

obtaining, by the one or more processors, metadata associated with the user;

determining, by the one or more processors and using a context component of the machine-learned skin condition classification model, an additional feature representation based on the user metadata;

generating, by the one or more processors, a unified representation of the one or more embeddings and the additional feature representation; and determining, by the one or more processors using a second portion of the machine-learned skin condition classification model, a skin condition classification for the portion of the user's skin, the skin condition classification produced by the second portion of the machine-learned skin condition classification model by processing the unified representation, wherein the skin condition classification identifies one or more skin conditions selected from a plurality of potential skin conditions.

12. The device of claim 11, wherein the one or more images include a plurality of images and the first portion of the machine learned classification model determines a plurality of embeddings for the plurality of images.

13. The device of claim 12, the operations further comprising:

combining, by the one or more processors, the plurality of embeddings to obtain a unified representation associated with the portion of the user's skin; and wherein the second portion of the machine-learned skin condition classification model determines a skin condition classification:

obtaining, by the one or more processors, metadata associated with the user;

determining, by the one or more processors using a context component of the machine-learned skin condition classification model, an additional feature representation based on the user metadata; and generating, by the one or more processors, a combination of the unified representation and the additional feature representation, wherein the skin condition classification is determined by the second portion of the machine-learned skin condition classification model by processing the combination of the unified representation and the additional feature representation.

14. The device of claim 11, wherein the user metadata includes demographic data associated with the user.

15. The device of claim 11, wherein the user metadata includes medical history data associated with the user.

16. The device of claim 11, wherein the skin condition classification comprises a differential diagnosis.

17. The device of claim 16, wherein the differential diagnosis identifies a plurality of potential skin conditions.

18. The device of claim 11, wherein the user metadata is obtained from a computing device associated with a user.

19. A computer-implemented method comprising:

accessing, by a computing system, historical skin condition data, the historical skin condition data including data representing a plurality of skin condition cases, each skin condition case including one or more images associated with the respective skin condition case;

adding, by the computing system, one or more diagnostic labels to one or more of the plurality of skin condition cases included in the historical skin condition data, wherein adding one or more diagnostic labels to a respective skin condition case includes:

receiving, by the computing system, a plurality of differential diagnoses from a plurality of labelers; and aggregating, by the computing system, the plurality of differential diagnoses to produce an aggregated differential diagnosis for the respective skin condition case, the aggregated differential diagnosis including two or more potential skin conditions;

providing, by the computing system, the one or more images associated with at least a subset of the plurality of skin condition cases as input to a skin condition classification model, the skin condition classification model having an initial set of weight values and producing a predicted differential diagnosis for each skin condition case in the subset of the plurality of skin condition cases as output;

evaluating, by the computing system, a difference between the predicted differential diagnosis produced as output of the skin condition classification model and the one or more diagnostic labels associated with the subset of the skin condition cases; and adjusting, by the computing system, one or more of the initial set of weight values based on the difference between the predicted differential diagnosis produced as output of the skin condition classification model and the one or more diagnostic labels associated with the subset of the skin condition cases.

20. The computer-implemented method of claim 19, wherein aggregating the plurality of differential diagnoses further comprises:

for a respective potential skin condition in the two or more potential skin conditions:

generating, by the computing system, a plurality of normalized confidence values for the respective potential skin condition, each respective normalized confidence value representing a confidence value from a particular labeler in the plurality of labelers;

generating, by the computing system, an average confidence value for a respective potential skin condition based on the plurality of normalized confidence values for the respective potential skin condition; and generating, by the computing system, the aggregated differential diagnosis for the respective skin condition case based on the average confidence value for each potential skin condition associated with the respective skin condition case.

* * * * *